US008127646B2

(12) United States Patent
Couvillion et al.

(10) Patent No.: US 8,127,646 B2
(45) Date of Patent: Mar. 6, 2012

(54) METHOD AND APPARATUS FOR PREPARING BONE GRAFTS, INCLUDING GRAFTS FOR CERVICAL INTERBODY FUSION

(76) Inventors: Roy J. Couvillion, Lafayette, LA (US); John E. Cobb, Lafayette, LA (US)

( * ) Notice: Subject to any disclaimer, the term of this patent is extended or adjusted under 35 U.S.C. 154(b) by 539 days.

(21) Appl. No.: 11/487,565

(22) Filed: Jul. 14, 2006

(65) Prior Publication Data
US 2008/0011137 A1  Jan. 17, 2008

(51) Int. Cl.
*A61B 17/32* (2006.01)
(52) U.S. Cl. .................. 83/34; 83/456; 83/763
(58) Field of Classification Search ........... 83/452, 83/454, 456, 459, 761–765; 606/87; 269/87, 269/87.2
See application file for complete search history.

(56) References Cited

U.S. PATENT DOCUMENTS

| | | | | |
|---|---|---|---|---|
| 1,307,397 A * | 6/1919 | Garlock | ............ | 83/762 |
| 1,426,026 A * | 8/1922 | Webster | ............ | 72/474 |
| 1,703,154 A * | 2/1929 | Lanzkron | ............ | 83/762 |
| 2,003,619 A * | 6/1935 | Williamson | ............ | 269/87.2 |
| 2,441,379 A * | 5/1948 | Zimmermann | ............ | 269/87 |
| 2,613,714 A * | 10/1952 | Miller | ............ | 83/762 |
| 3,768,797 A * | 10/1973 | Kartasuk et al. | ............ | 269/283 |
| 4,325,543 A * | 4/1982 | York | ............ | 269/295 |
| 4,779,503 A * | 10/1988 | Mitchell | ............ | 83/796 |
| 4,854,206 A * | 8/1989 | Wilfong | ............ | 83/745 |
| 4,960,269 A * | 10/1990 | Fong | ............ | 269/87.2 |
| 5,042,983 A | 8/1991 | Rayhack | | |
| 5,083,759 A * | 1/1992 | Pollak et al. | ............ | 269/134 |
| 5,176,685 A | 1/1993 | Rayhack | | |
| 5,817,097 A | 10/1998 | Howard et al. | | |
| 6,152,435 A * | 11/2000 | Snell | ............ | 269/43 |
| 6,648,894 B2 * | 11/2003 | Abdelgany et al. | ............ | 606/79 |
| 6,676,662 B1 * | 1/2004 | Bagga et al. | ............ | 606/87 |
| 2002/0138078 A1 | 9/2002 | Chappuis | | |
| 2004/0034360 A1 * | 2/2004 | Dalton | ............ | 606/87 |
| 2004/0034361 A1 | 2/2004 | Dalton | | |
| 2004/0034362 A1 | 2/2004 | Abdelgany et al. | | |
| 2004/0220578 A1 | 11/2004 | Bagga et al. | | |

OTHER PUBLICATIONS

Albee, Fred H. "Bone Surgery with Machine Tools". Apr. 1936. Scientific American.*

* cited by examiner

*Primary Examiner* — Edward Landrum
(74) *Attorney, Agent, or Firm* — Ted M. Anthony

(57) ABSTRACT

A base having a substantially planar surface, a plurality of upright fingers, and a blade guide that can be adjustably positioned along the planar surface. The blade guide can be biased toward the upright fingers to secure a section of donor bone between the blade guide and the upright fingers. Aligned openings in the blade guide and planar surface, as well as the gaps between the upright fingers, permit precision cutting of a donor bone section to prepare a graft having a desired size and/or configuration.

5 Claims, 7 Drawing Sheets

METHOD AND APPARATUS FOR PREPARING BONE GRAFTS, INCLUDING GRAFTS FOR CERVICAL INTERBODY FUSION

BACKGROUND OF THE INVENTION

1. Field of the Invention

The present invention relates to a method and apparatus for preparing bone grafts for use in the repair, replacement, and/or augmentation of various portions of animal or human skeletal systems. More particularly, the present invention relates to prepared bone grafts, guides for forming bone grafts and methods for forming bone grafts.

2. Brief Description of the Prior Art

Several procedures involve the use and implantation of bone into an animal or human body. Generally, benefits of implanted bone include, but are not limited to, providing support, promoting healing, filling cavities, separating or spacing bony elements such as vertebral bodies, promoting fusion, and stabilizing the site of fractures.

Although the use of bone grafts is not limited to the spine, bone grafts are frequently implanted during certain surgical procedures to promote surgical decompression and/or stabilization of the spine. Such procedures include, but are not necessarily limited to, spinal discectomy with fusion and postcorpectomy reconstruction. In such procedures, autogenic, allogenic or xenogenic bone or synthetic material can be used to provide structural support in voids where diseased or damaged tissue or bone has been removed from the spine.

During such procedures, it is often critically important that the size and geometry of the implanted bone be consistent with the void into which said implanted bone is ultimately introduced. Put another way, the success of such procedures frequently depend, at least in large part, on the degree to which the size and geometry of an implanted bone section matches the void that will receive said bone section.

Practitioners generally have a number of different options available when choosing inter-body fusion implants. Such implants can basically be segregated into two groups: mechanical devices and actual bone. When using actual bone implants, practitioners can utilize pre-processed bone grafts that are currently available in a number of different configurations and geometries. Alternatively, practitioners can prepare implant grafts intra-operatively using a section of donor bone. Autogenic grafts, by their very nature, must be prepared intra-operatively.

Some practitioners prefer intra-operative graft preparation. Even when measurements translated from pre-operative non-invasive imagery are used to determine appropriate graft geometry, intra-operative measurement is still required to ensure proper fit of a particular graft. Intra-operative bone graft preparation allows a surgeon to customize an implant to fit a particular application. Some practitioners will even modify pre-processed bone grafts prior to insertion.

Alternatively, a section of a bone can be taken directly from the patient receiving the implant. In such cases, a "donor" bone (known as an "autograft") is harvested from another part of a patient's body and used as in implant during the surgical procedure. However, the autograft is frequently longer and/or shaped differently than the required bone implant. Thus, the donor bone often must be cut to precise lengths and/or at precise angles.

When using a patient's donor bone, it is frequently necessary to form required bone implant sections directly in the intra-operative environment such as the operating room itself. Moreover, multiple graft implants are frequently required. To minimize trauma associated with autographic bone harvesting, it is typically advantageous to form multiple graft sections from the same donor bone.

Thus, there is a need for a simple, inexpensive and effective method and apparatus for the manufacture of bone implants directly in an intra-operative environment. The subject apparatus should allow a surgeon to produce, and thereafter faithfully reproduce, grafts with a high degree of precision. The subject apparatus should be robust, durable, easy to use, consistent with surgical environment(s) and compatible with existing cutting tools.

SUMMARY OF THE PRESENT INVENTION

The present invention comprises a method and apparatus for forming bone grafts from autogenic, allogenic or xenogenic bone. The device of the present invention can be used in virtually any environment including intra-operative environments such operating rooms and/or other facilities used for performing surgical procedures. The present invention can be beneficially sized to accommodate different sizes and shapes of donor bones, and can be easily cleaned and/or autoclaved for repeated use. Further, the present invention permits formation of bone grafts by a single operator, including an operator having compromised dexterity and/or hand strength. Nonetheless, the present invention also allows an assistant or secondary operator to aid in its use by providing lighting, irrigation and the like.

In one preferred embodiment, the present invention comprises a base having a substantially planar surface. For most applications, said base has a substantially horizontal orientation. An elongate upright member extends along one side of said base. In the preferred embodiment, a surface is defined in the transition between the planar surface of the base and said upright member; the geometry of the surface is beneficially configured to receive the outer (generally cylindrical) surface of a donor bone. In the preferred embodiment, such transition surface forms an angle of approximately ninety degrees.

At least one track is formed on the planar surface of said base, wherein said at least one track is oriented substantially perpendicular to the longitudinal axis of said upright member (as well as the surface formed in the transition between said planar surface and said upright member). An opening extends through said upright member, surface and substantially planar surface of said base to define a plurality of upright fingers. In the preferred embodiment, said upright fingers are offset relative to said planar surface and upright member, and are aligned with the at least one track formed in the planar surface of the base.

A moveable blade guide is slidably received within said at least one track of said base. Said blade guide can travel along said substantially planar base within said at least one track and can be selectively positioned along said planar surface of said base relative to said upright fingers. Said blade guide further has a bone holder and a plurality of slots extending through said bone holder. In the preferred embodiment, said bone holder defines a curved surface having a shape and configuration that can accommodate the outer (generally cylindrical) surface of a donor bone. In the preferred embodiment, a plurality of ribs is disposed on said curved surface, and means are provided for biasing said blade guide toward said plurality of upright fingers.

A section of donor bone can be placed on said base against said upright fingers. Thereafter, said blade guide can be moved within said at least one track until the blade guide is secured in a desired position against such donor bone. In this configuration, the donor bone is secured between said upright fingers and bone holder of the blade guide. Once a donor bone is secured in place, precision cuts can be made to said donor bone in order to prepare bone grafts having desired shapes and sizes.

Any number of different means for biasing said blade guide toward said upright fingers can be used. However, in the preferred embodiment, the means for biasing said blade guide toward said upright fingers comprises a threaded screw mechanism. In such configuration, a threaded bore, oriented substantially parallel to said at least one track, is disposed in said base. A spacing member having an aperture is installed between said blade guide and threaded bore; the aperture of said spacing member is beneficially aligned with said threaded bore.

A bolt having a head and threads is inserted through the aperture of the spacing member and is threadedly received within said threaded bore. As the threads of said bolt engage with the threads of said threaded bore of said base, the head of said bolt travels generally in the direction of said upright fingers. The head of said bolt acts upon said spacing member, which in turn acts upon the blade guide, thereby biasing said blade guide within the track(s) of said base toward said upright fingers. This action forces said blade guide toward said upright fingers, in turn allowing a section of donor bone situated on said upright fingers to be secured between the bone holder of the blade guide and the upright fingers of the base.

In one embodiment of the invention, a bone graft having parallel faces can be prepared. Slots formed in the blade guide allow a cutting device, such as a saggital saw blade well known in the art, to move freely within a plane of radical oscillation. Said slots can guide the cutting edge of such a blade through a donor bone within the desired plane. In this embodiment, such slots are situated at varied but fixed spacing intervals and at normal angles relative to the longitudinal axis of said donor bone. Openings extending into the base between said upright fingers are aligned with the slots of the blade guide, thereby allowing a cutting blade to freely exit the bone. Moreover, because multiple aligned openings are formed in the blade guide and base, two faces of a bone graft can be completed without repositioning a donor bone.

In another embodiment of the invention, a bone graft with convergent oblique faces can be prepared. An alternative blade-guide having slots formed at converging oblique angles relative to the longitudinal axis of a donor bone can be used. Because multiple aligned slots are formed in the blade guide and base, two faces of a bone graft can be completed without repositioning a donor bone.

In yet another embodiment of the invention, a graft combining right and oblique faces can be prepared. An alternative blade-guide having slots cut at both normal and oblique angles relative to the longitudinal axis of a donor bone can be used. Again, because multiple aligned slots are formed in the blade guide and base, two faces of a bone graft can be completed without repositioning a donor bone.

The device of the present invention is robust and can be used in virtually any environment, including intra-operative environments such as those operating rooms and/or other facilities used for performing surgical procedures. The components of the present invention can be easily reconfigured as desired to fit different types of donor bones, and can be easily cleaned and/or autoclaved for repeat use.

DETAILED DESCRIPTION OF A PREFERRED EMBODIMENT OF THE INVENTION

Figure 1:
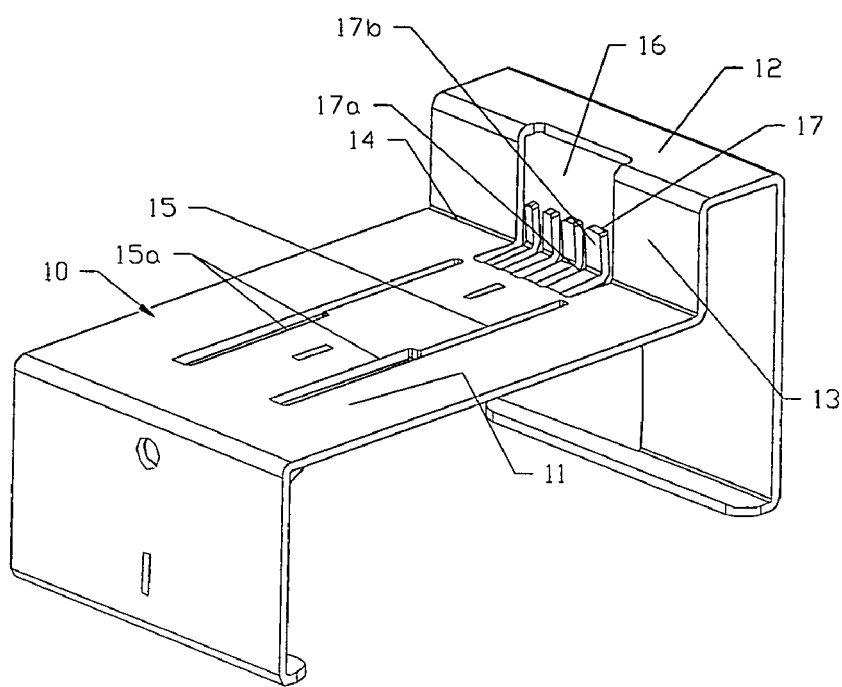
FIG. 1 depicts a perspective view of the base of the cutting apparatus of the present invention.

Referring to the drawings, FIG. 1 depicts a perspective view of base 10 of the apparatus of the present invention. Base 10 has substantially planar surface 11. In most applications, substantially planar surface 11 is situated in a substantially horizontal orientation. Elongate upright member 12 extends along one side of said base 10. In the preferred embodiment, base 10 is formed from sheet stock or other similar material so that upright member 12 is not solid. Upright member defines substantially vertical surface 13, while junction 14 forms the transition between substantially planar surface 11 and substantially vertical surface 13 of upright member 12. In the preferred embodiment, junction 14 forms a right angle; however, the shape and/or radius of curvature of junction 14 can be beneficially configured to accommodate the outer (generally cylindrical) surface of a donor bone.

Still referring to FIG. 1, slotted tracks 15 are disposed along planar surface 11 of said base 10. In the preferred embodiment, tracks 15 are oriented in a direction that is substantially perpendicular to the longitudinal axis of upright member 12 (as well as junction 14), and have enlarged sections 15a opposite upright member 12. Opening 16 is formed in upright member 12 (including junction 14 and substantially vertical surface 13) and substantially planar surface 11 of base 10. In the preferred embodiment, upright fingers 17 are formed along a portion of substantially planar surface 11 of base 10; said fingers 17 are aligned with opening 16. Said fingers 17 have horizontal components 17A and vertical components 17b and are integrally formed with planar surface 11. Further, said fingers 17 beneficially stand out relative to substantially planar surface 11, junction 14 and substantially vertical surface 13.

Figure 2:
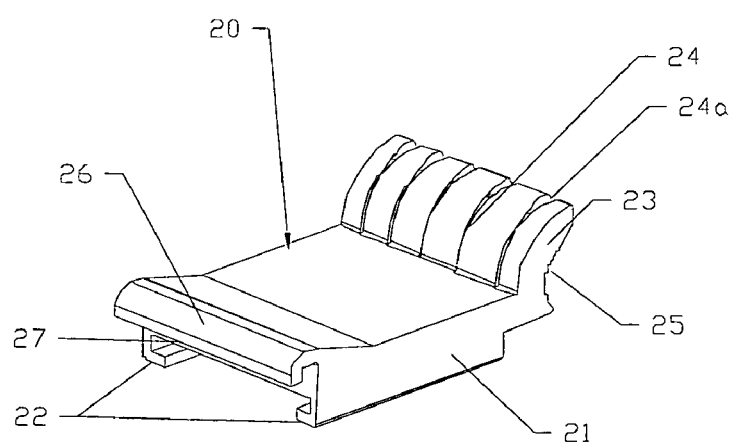
FIG. 2 depicts a perspective view of a blade guide of the present invention.

FIG. 2 depicts a perspective view of a movable blade guide 20 of the present invention. Blade guide 20 comprises body section 21 having opposing L-shaped track mounts 22 and bone holder 23. In the preferred embodiment, bone holder 23 defines inner surface 25 having a geometry that can accommodate the outer surface of a section of donor bone. In most cases, inner surface 25 is curved to accommodate the generally cylindrical surface of a donor bone; however, it is to be observed that surface 25 can have any number of different shapes to match a particular donor bone to be cut. A plurality of slots 24 extends through bone holder 23. In the preferred embodiment, slots 24 include wider areas 24a along the leading edge of bone holder 23. Bracket member 26 defining lip 27 extends from body section 21 of blade guide 20 along the opposite side of said blade guide 20 from bone holder 23.

Figure 3:
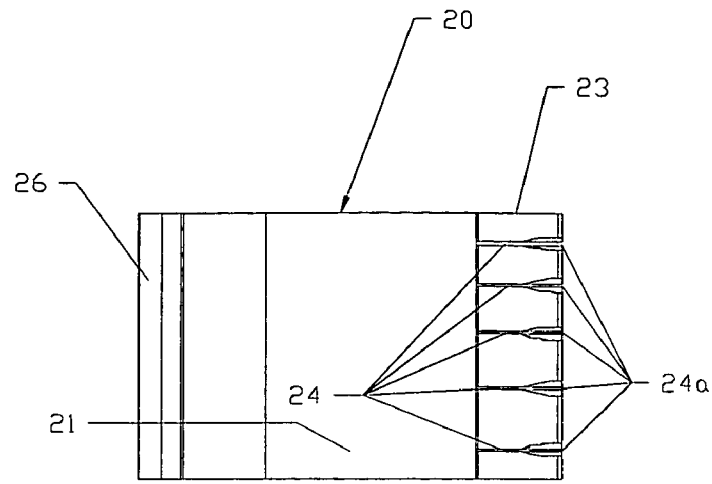
FIG. 3 depicts an overhead view of a blade guide of the present invention with slots formed parallel to each other.
Figure 4:
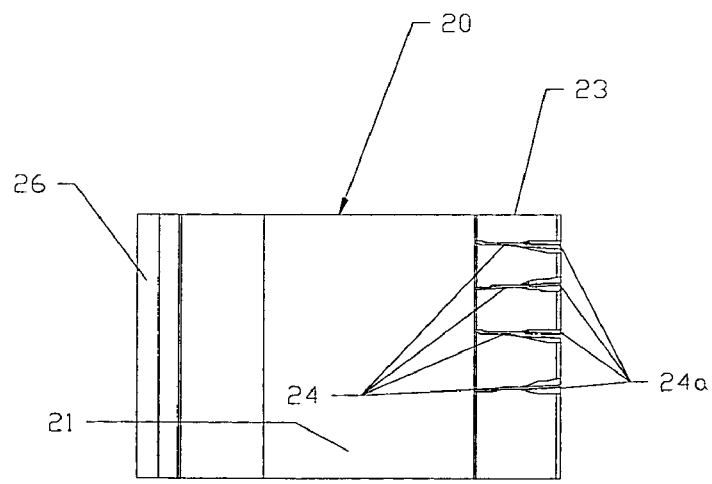
FIG. 4 depicts an overhead view of a blade guide of the present invention with slots formed at acute angles relative to each other.

FIG. 3 depicts an overhead view of a blade guide 20 of the present invention. Bracket member 26 extends from body section 21 of blade guide 20 along the opposite side of blade guide 20 from bone holder 23. A plurality of slots 24 extends through bone holder 23. In FIG. 3, slots 24 are oriented parallel to one another and at right angles relative to the longitudinal axis of bone holder 23. In the preferred embodiment, slots 24 have wider areas 24a at the leading edge of bone holder 23. FIG. 4 depicts an overhead view of a blade guide 20 of the present invention that is generally identical to the blade guide depicted in FIG. 3, except that slots 24 are oriented at oblique angles relative to one another. It is to be observed that such slots 24 can be oriented any number of ways, as desired, to accomplish a particular graft geometry.

Figure 5:
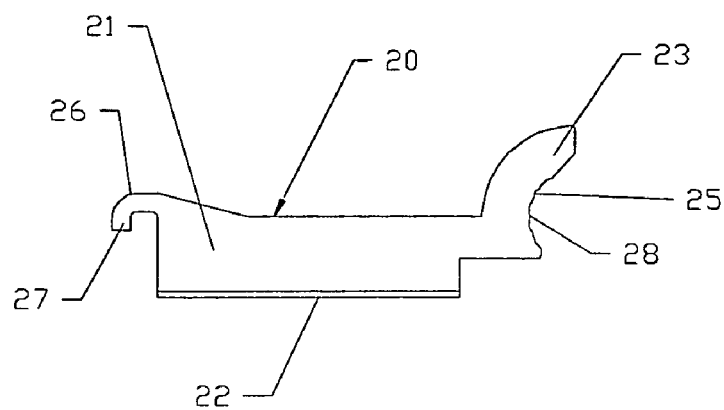
FIG. 5 depicts a side view of a blade guide of the present invention.

FIG. 5 depicts a side view of blade guide 20 of the present invention having body section 21 and bone holder 23. Bracket member 26 defining lip 27 extends from body section 21 of blade guide 20 along the opposite side of blade guide 20 from bone holder 23. Bone holder 23 defines curved inner surface 25 having a geometry that can beneficially accommodate the outer (generally cylindrical) surface of a donor bone. A plurality of ribs 28 can be disposed along inner surface 25 of bone holder 23. Optional ribs 28 improve the ability of bone holder 23 to secure a section of donor bone held by such bone holder 23 and prevent movement of such donor bone.

Figure 6:
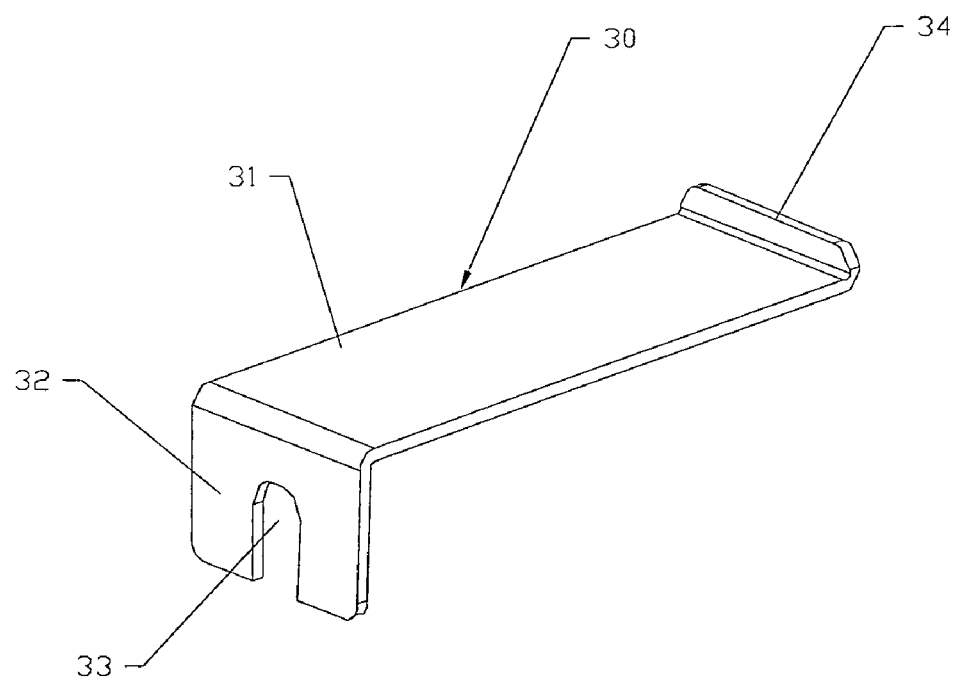
FIG. 6 depicts a perspective view of a spacing member of the present invention.
Figure 7:
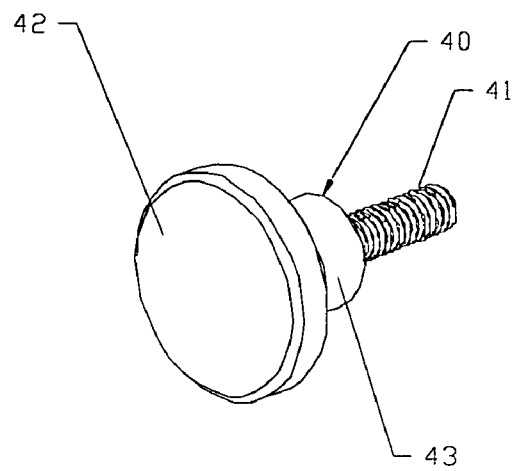
FIG. 7 depicts a perspective view of a biasing bolt of the present invention.

FIG. 6 depicts a perspective view of a spacing member 30 of the present invention. Spacing member 30 comprises body section 31, face member 32 and upright lip 34. Aperture 33 extends through face member 32. FIG. 7 depicts a perspective view of biasing bolt 40 of the present invention. Biasing bolt 40 has threaded bolt section 41, as well as head 42. In the preferred embodiment, biasing bolt 40 also has body section 43 having a larger diameter than that of aperture 33 in face member 32 of spacing member 30.

Figure 8:
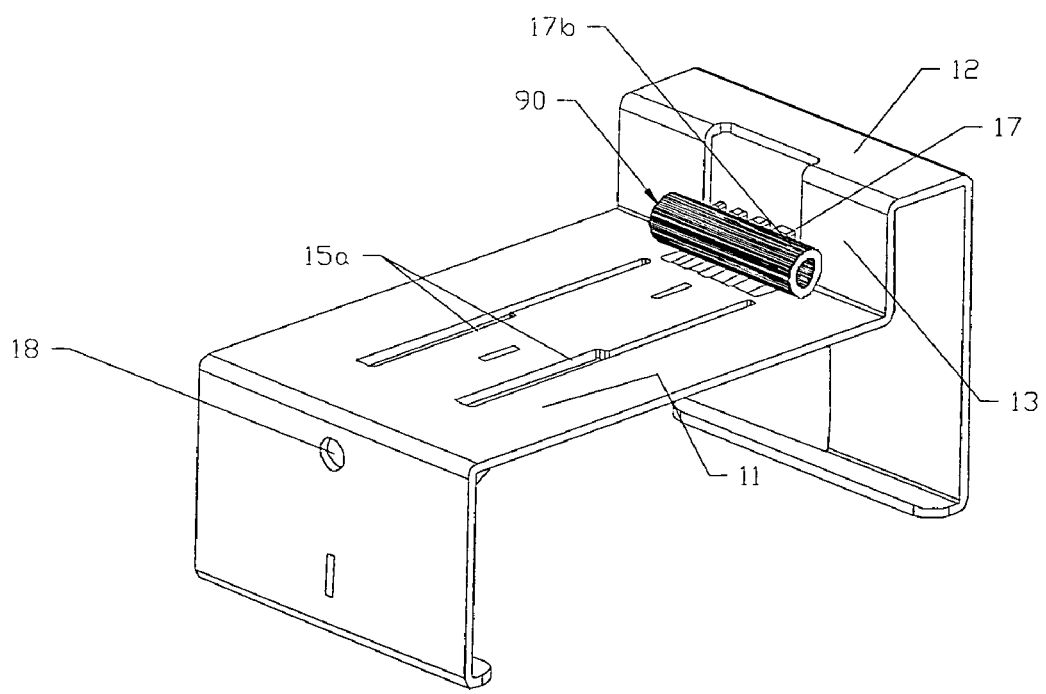
FIG. 8 depicts a perspective view of the base member of the present invention having a section of donor bone disposed on said base member.

FIG. 8 depicts a perspective view of base member 10 of the present invention having a section of donor bone 90 disposed on said base member. Donor bone section 90 is beneficially placed generally on junction 14 formed between planar surface 11 and substantially vertical surface 13 of upright member 12. More particularly, said donor bone section 90 is disposed across upright fingers 17. In this configuration, donor bone section 90 is generally aligned with tracks 15. Threaded bore 18 is disposed in base 10, and is ideally positioned between tracks 15. The longitudinal axis of threaded bore 18 is substantially parallel to tracks 15.

Figure 9:
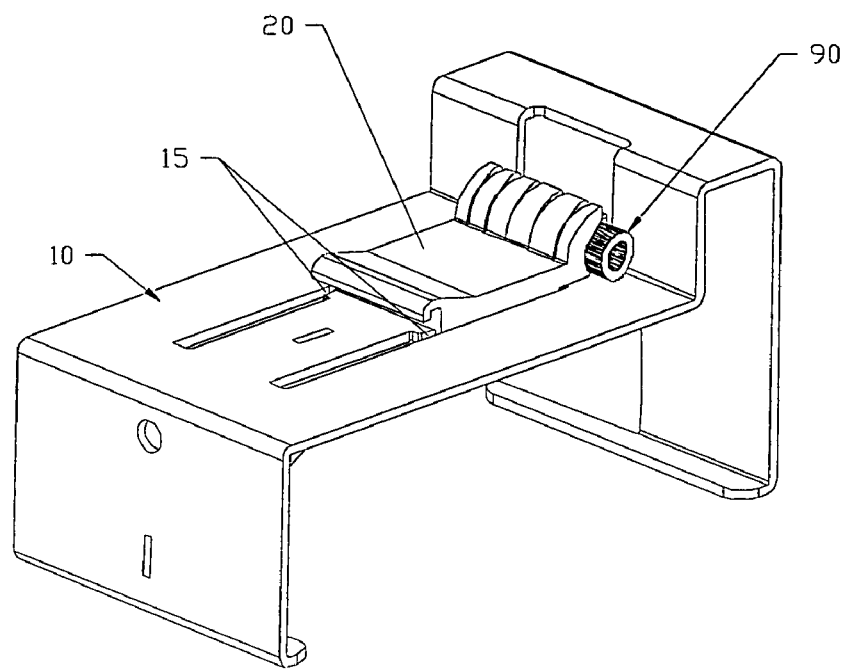
FIG. 9 depicts a perspective view of the base member of the present invention having a section of donor bone disposed on said base member with a blade guide installed.

FIG. 9 depicts a perspective view of base member 10 and blade guide 20 positioned against donor bone section 90. L-shaped track mounts 22 (not shown in FIG. 9) of blade guide 20 are inserted into openings 15a of tracks 15, so that blade guide 20 is slidably disposed within tracks 15 of base 10. Blade guide 20 can travel within tracks 15 along substantially planar surface 11 and can be selectively positioned along planar surface 11 of base 10 relative to fingers 17 (not shown in FIG. 9) and donor bone section 90.

Figure 10:
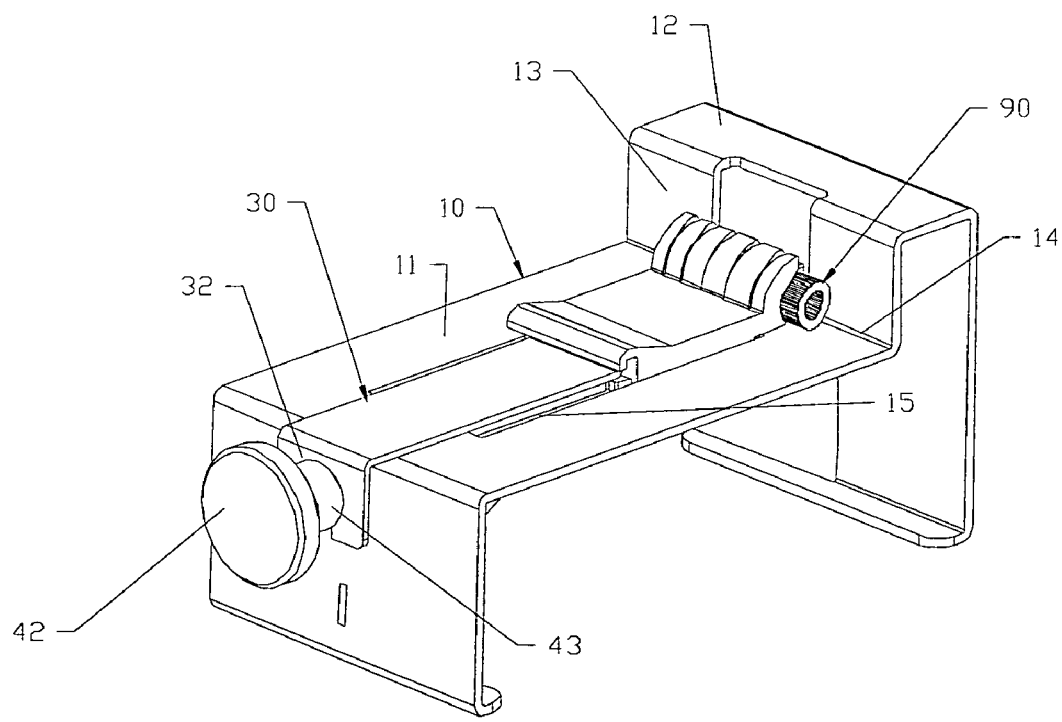
FIG. 10 depicts a perspective view of the cutting apparatus of the present invention holding a section of donor bone.

FIG. 10 depicts a perspective view of the cutting apparatus of the present invention securely holding a section of donor bone. Extension 34 (not shown in FIG. 10) of spacing member 30 is received under lip 27 of bracket member 26 of blade guide 20, thereby joining said spacing member 30 to blade guide 20. Donor bone section 90 is beneficially placed generally on junction 14 formed between planar surface 11 and substantially vertical surface 13 of upright member 12. More particularly, said donor bone section 90 is disposed across upright fingers 17. In this configuration, donor bone section 90 is generally aligned with tracks 15. L-shaped track mounts 22 (not shown in FIG. 10) of blade guide 20 are inserted into openings 15a of tracks 15, so that blade guide 20 is slidably disposed within tracks 15 of base 10. Blade guide 20 can travel within tracks 15 along substantially planar surface 11 and can be selectively positioned along planar surface 11 of base 10 relative to fingers 17 (not shown in FIG. 10) and donor bone section 90.

Figure 11:
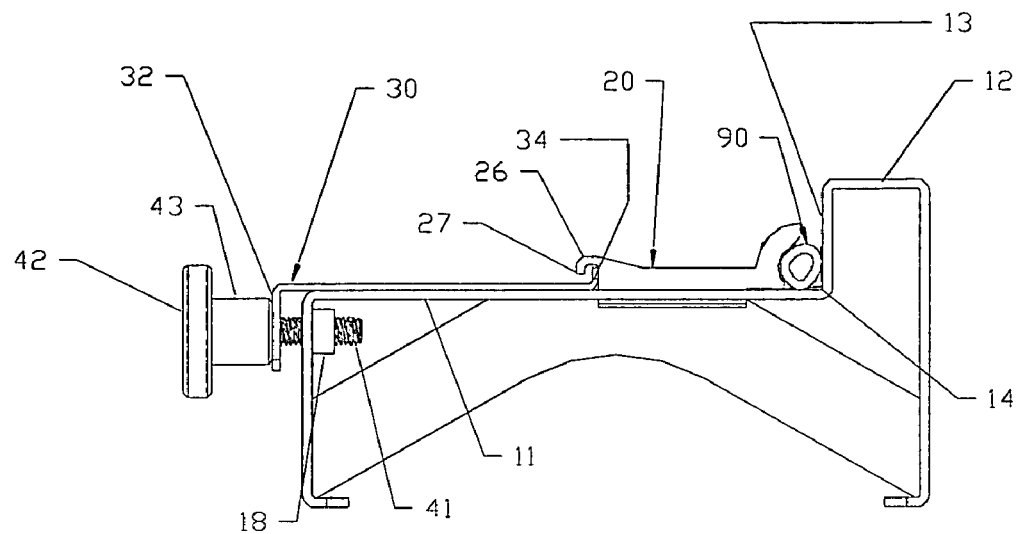
FIG. 11 depicts a side view of the cutting apparatus of the present invention holding a section of donor bone.

FIG. 11 depicts a side view of the cutting apparatus of the present invention holding a section of donor bone 90. Donor bone section 90 is beneficially seated within junction 14 formed between substantially planar surface 11 and substantially vertical surface 13 of upright member 12. Specifically, donor bone section 90 rests on fingers 17 (not shown in FIG. 11) of base 10. In this configuration, donor bone section 90 is generally aligned with tracks 15 in substantially planar surface 11 of base 10.

Still referring to FIG. 11, blade guide 20 is slidably received within tracks 15 of base 10 and can be selectively positioned along planar surface 11 of base 10 relative to fingers 17 and donor bone section 90. Extension 34 of spacing member 30 is received under lip 27 of bracket member 26 of blade guide 20, thereby joining said spacing member 30 to blade guide 20. Threaded bolt section 41 of biasing bolt 40 extends though aperture 33 (not shown in FIG. 11) of spacing member 30 and is threadably received within threaded bore 18 of base 10. As head 42 of biasing bolt 40 is rotated, threaded bolt section 41 advances within threaded bore 18, forcing body section 43 of biasing bolt 40 into face member 32 of spacing member 30. Spacing member 30 in turn forces blade guide 20 towards donor bone section 90, securing said donor bone section in compression against fingers 17 (not shown in FIG. 11).

Figure 12:
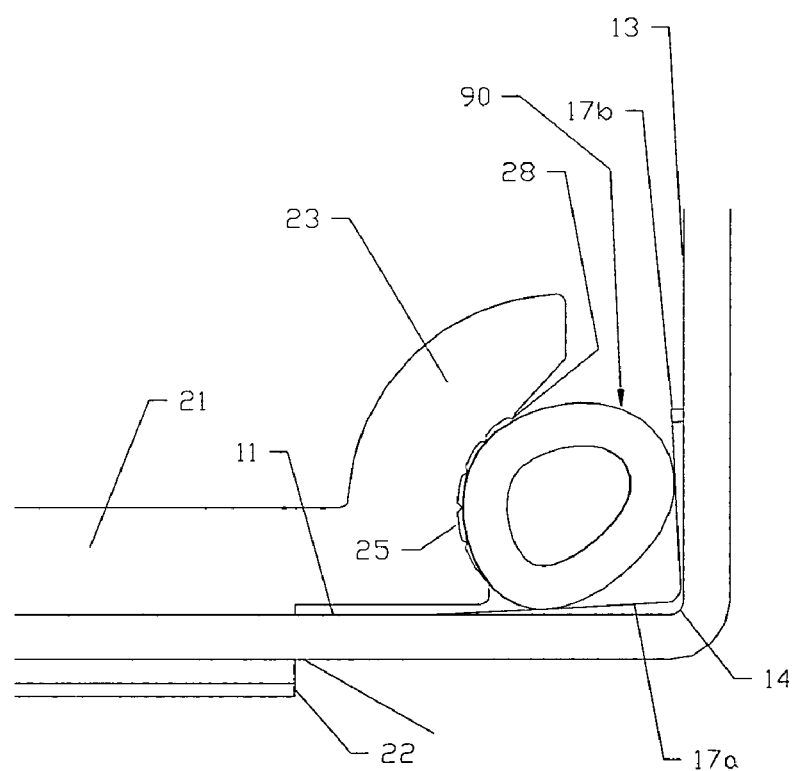
FIG. 12 depicts a detailed side view of the cutting apparatus of the present invention holding a section of donor bone.

FIG. 12 depicts a detailed cross-sectional view of the cutting apparatus of the present invention holding a section of donor bone. Donor bone section 90 having an irregular (that is, not perfectly round) shape is beneficially placed on junction 14 formed between planar surface 11 and substantially vertical surface 13 of upright member 12. In this position, a portion of said donor bone section 90 contacts lower section 17a and upper section 17b of upright fingers 17. In the preferred embodiment, said upright fingers stand proud—that is, stand out—relative to substantially planar surface 11 and substantially vertical surface 13 and have some flexibility. As such, said upright fingers provide a resilient cradle-like surface to beneficially support donor bone section 90. As blade guide 20 is biased against donor bone section 90, curved surface 25 of bone holder 23 acts to secure donor bone section 90 in place between bone holder 23 and upright fingers 17. Optional ribs 28 disposed on curved surface 25 help to secure donor bone section 90 and further prevent unwanted movement of said donor bone section.

Figure 13:
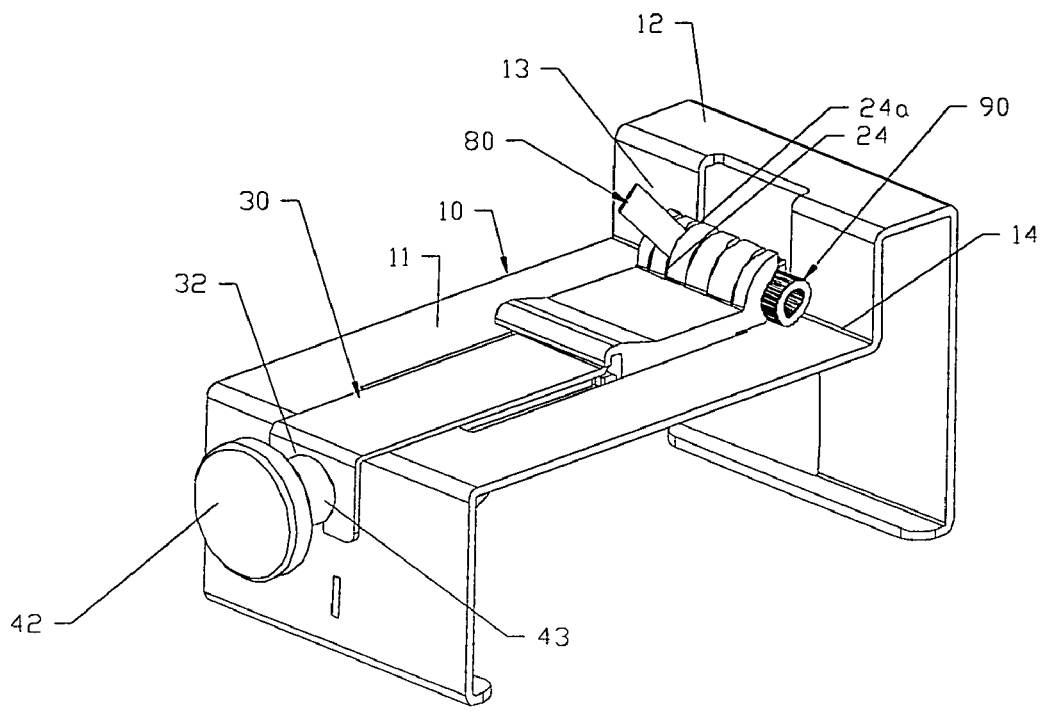
FIG. 13 depicts a perspective view of the cutting apparatus of the present invention holding a section of donor bone while being cut.

FIG. 13 depicts a perspective view of the cutting apparatus of the present invention holding donor bone 90 while being cut. Once donor bone section 90 is secured in place using the apparatus of the present invention as set forth in detail above, precision cuts can be made to donor bone section 90 in order to prepare bone grafts having desired shapes and sizes. Specifically, blade 80 is inserted through slots 24 of blade guide 20 to cut donor bone section 90. Slots 24 allow blade 80 (which can be any number of cutting devices known in the art such as, for example, a saggital saw blade) to move freely within a plane of radical oscillation. Slots 24, ideally having wider opening 24a at the leading edge of bone holder 23 to guide a saw blade into such slots 24, effectively guide the cutting edge of blade 80 through a donor bone section 90 within the desired plane. Said blade 80 can also extend into gaps existing between upright fingers 17 to ensure thorough cutting of donor bone section 90.

In one embodiment of the present invention, slots 24 are situated at fixed spacing intervals relative to one another, and at normal angles relative to the longitudinal axis of donor bone section 90. Openings are also are formed between upright fingers 17 and are aligned with slots 24 of blade guide 20, thereby allowing blade 80 to extend into such openings between upright fingers 17 and freely exit donor bone section 90 upon completion of a cut. Because multiple aligned slots 24 are formed in blade guide 20, two faces of a bone graft can be prepared without repositioning donor bone section 90.

In another variation of the invention, a bone graft with convergent oblique faces can be prepared. An alternative blade guide having slots formed at converging oblique angles relative to the longitudinal axis of donor bone section 90 can be used instead of blade guide 20 depicted in FIG. 13. In yet another embodiment of the invention, a graft combining right and oblique faces can be prepared. An alternative blade guide having slots cut at both normal and oblique angles relative to the longitudinal axis of donor bone section 90 can be used instead of bone guide 20 depicted in FIG. 13.

Once donor bone section 90 is secured in place, precision cuts can be made to donor bone section 90 in order to prepare bone graft(s) having desired shapes and sizes. Blade 80 is inserted through slots 24 of blade guide 20 to cut donor bone section 90. Slots 24 guide the cutting edge of blade 80 through donor bone section 90 within the desired plane.

Figure 14:
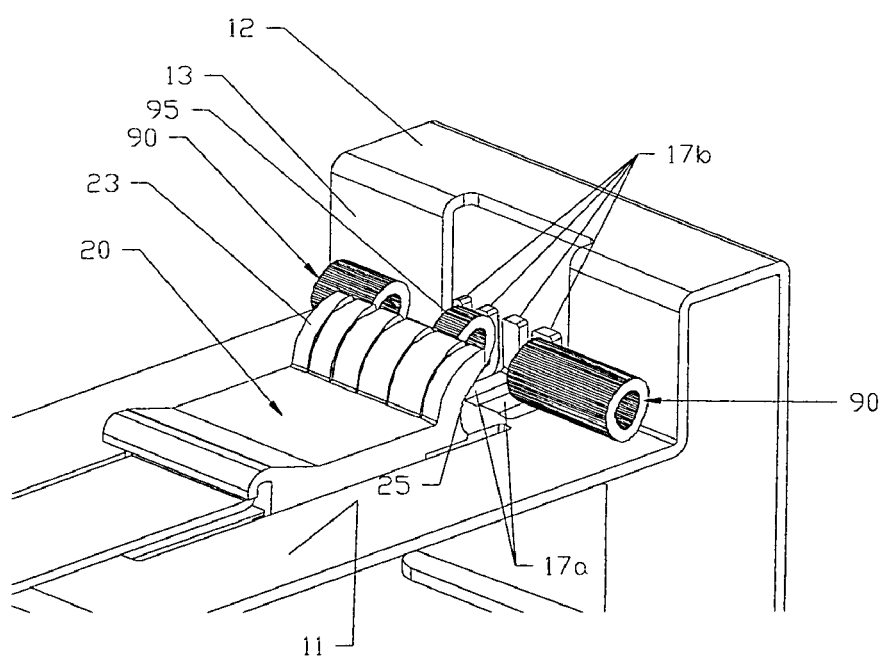
FIG. 14 depicts a perspective view of the cutting apparatus of the present following the cutting of a section of donor bone.

FIG. 14 depicts a perspective view of the cutting apparatus of the present following the cutting of donor bone section 90. Following such cutting operations, biasing bolt 40 (not shown in FIG. 14) is partially or fully unscrewed and blade guide 20 is removed from donor bone section 90. As depicted in FIG. 14, donor bone section 90 has been cut to form bone graft section 95, having a desired shape and size. During the cutting process, bone graft section 95, which is much smaller than donor bone section 90, is nonetheless supported by certain independently-acting and resilient upright fingers 17. Bone graft section 95 can be utilized in connection with any number of beneficial medical procedures including, but not necessarily limited to, surgical procedures.

The device of the present invention is robust and can be used in virtually any environment, including intra-operative environments such as those operating rooms and/or other facilities used for performing surgical procedures. The components of the present invention can be easily reconfigured and/or interchanged as desired to accommodate different sizes and types of donor bones, and can be easily cleaned and/or autoclaved for repeat use.

The above disclosed invention has a number of particular features which should preferably be employed in combination, although each is useful separately without departure from the scope of the invention. While the preferred embodiment of the present invention is shown and described herein, it will be understood that the invention may be embodied otherwise than herein specifically illustrated or described, and that certain changes in form and arrangement of parts and the specific manner of practicing the invention may be made within the underlying idea or principles of the invention.

What is claimed is:

1. A method for forming bone grafts comprising:
   a. placing an elongate donor bone having a longitudinal axis on a base having:
      i. a substantially planar horizontal surface having a first end and a second end;
      ii. an upright member extending along said first end of said substantially planar horizontal surface, wherein said upright member defines a substantially planar vertical surface having an opening, and said vertical surface is oriented substantially perpendicular to said substantially planar horizontal surface;
      iii. an upright finger extending from said substantially planar horizontal surface, wherein said upright finger has first and second sides, is oriented substantially perpendicular to the longitudinal axis of said donor bone and is disposed within said opening in said substantially planar vertical surface of said upright member; and
      iv. a blade guide slidably disposed on said substantially planar horizontal surface of said base having a forward surface adapted to contact said donor bone, a plurality of ribs disposed on said forward surface, and first and second substantially vertical slots extending through said blade guide, wherein each of said first and second slots is open at its top, closed at its bottom, and wider at its top than at its bottom;
   b. biasing said blade guide against said elongate donor bone, wherein said upright finger is disposed between said first and second substantially vertical slots of said blade guide;
   c. passing a blade of a reciprocating saw through said first substantially vertical slot of said blade guide to cut said donor bone adjacent to said first side of said upright finger; and
   d. passing said blade through said second substantially vertical slot of said blade guide to cut said donor bone adjacent to said second side of said upright finger.

2. The method of claim 1, wherein said forward surface of said blade guide has a concave shape facing said donor bone.

3. The method of claim 1, wherein said upright finger further comprises:
   a. a first section oriented in substantially the same place as said substantially planar base; and
   b. a second section extending at an angle from the first section.

4. The method of claim 3, wherein the angle formed between said first and second sections is ninety degrees.

5. The method of claim 3, wherein the angle formed between said first and second sections is less than ninety degrees.

* * * * *